(12) United States Patent
Holt et al.

(10) Patent No.: US 8,020,457 B2
(45) Date of Patent: Sep. 20, 2011

(54) APPARATUS FOR USE IN SAMPLE MONITORING

(75) Inventors: Mark Wayne Holt, Emmaus, PA (US); William Howard Eberhardt, Cherry Hill, NJ (US)

(73) Assignee: Babcock & Wilcox Power Generation Group, Inc., Barberton, OH (US)

( * ) Notice: Subject to any disclaimer, the term of this patent is extended or adjusted under 35 U.S.C. 154(b) by 483 days.

(21) Appl. No.: 12/188,672

(22) Filed: Aug. 8, 2008

(65) Prior Publication Data

US 2010/0031729 A1    Feb. 11, 2010

(51) Int. Cl.
*G01N 1/22* (2006.01)

(52) U.S. Cl. .................................. 73/863.11

(58) Field of Classification Search .......... 73/863.11, 73/863.81, 863.83
See application file for complete search history.

(56) References Cited

U.S. PATENT DOCUMENTS

| | | | | |
|---|---|---|---|---|
| 3,960,500 A | * | 6/1976 | Ross et al. | 422/62 |
| 4,974,453 A | | 12/1990 | Hohorst | 73/863.11 |
| 6,539,312 B1 | | 3/2003 | Nimberger et al. | 702/24 |
| 2008/0017033 A1 | * | 1/2008 | Charrue et al. | 95/228 |
| 2010/0213363 A1 | * | 8/2010 | Nakajima et al. | 250/281 |

FOREIGN PATENT DOCUMENTS

| GB | 1486098 | | 9/1977 |
|---|---|---|---|
| GB | 2336669 A | | 10/1999 |
| JP | 2000074798 | | 3/2000 |
| JP | 2000074798 A | * | 3/2000 |

OTHER PUBLICATIONS

GB Search Report for Patent Application No. GB0913092.3; Date of Search Oct. 14, 2009.

* cited by examiner

*Primary Examiner* — Hezron E Williams
*Assistant Examiner* — Tamiko Bellamy
(74) *Attorney, Agent, or Firm* — Eric Marich

(57) ABSTRACT

An apparatus for use in a sample monitoring system is provided and includes a first enclosure configured to enclose a probe body into which the sample is drawn, a sensor coupled to the probe body and configured to sense a chemical composition of the sample and at least one first heater configured to heat an interior of the first enclosure, a second enclosure configured to enclose a pump coupled to the probe body and configured to draw the sample therein and a second heater configured to heat the pump, and a third enclosure configured to enclose a pump motor configured to control an operation of the pump and to support heating controlling units configured to control the at least one first heater and the second heater.

17 Claims, 3 Drawing Sheets

APPARATUS FOR USE IN SAMPLE MONITORING

BACKGROUND OF THE INVENTION

1. Field of the Invention

Aspects of the present invention are directed to an apparatus for use in sample monitoring.

2. Description of the Background

For the continuous emissions monitoring of oxygen on a hot wet basis for the power utility industry, the zirconium oxide sensor is commonly used. Such a sensor can either be placed directly in a stack and be used for in-situ monitoring of the oxygen therein on a hot wet basis or used as part of an extractive method for use in an extractive measurement system. In such an extractive method, an exhaust sample is transported from the stack using a heated sampling system to an oxygen sensor.

When the sample is monitored using an extractive measurement system, it is critical that the temperature of the sample in and around the sensor be stably maintained by heated components of the system and that no condensation of moisture in the sample occurs. If the temperature of the sample in and around the sensor is not stable, the oxygen measurements will be performed inaccurately. At the same time, the heated components of the extractive measurement system must not pose a risk of, e.g., fire or burn damage, to the operator.

It has been seen, however, that current extractive measurement systems may not reliably maintain the temperature of the sample in and around the sensor and also fail to sufficiently protect the operator. Indeed, in some current systems, a sensor box is heated via trace wiring and includes a heated pump that may be heated to a temperature that could uncontrollably exceed a performance rating for the wiring. Moreover, an exterior of the sensor box can also be heated to an extreme degree and thereby pose a danger to the operator.

SUMMARY OF THE INVENTION

In accordance with an aspect of the invention, an apparatus for use in a sample monitoring system is provided and includes a first enclosure configured to enclose a probe body into which the sample is drawn, a sensor coupled to the probe body and configured to sense a chemical composition of the sample and at least one first heater configured to heat an interior of the first enclosure, a second enclosure configured to enclose a pump coupled to the probe body and configured to draw the sample therein and a second heater configured to heat the pump, and a third enclosure configured to enclose a pump motor configured to control an operation of the pump and to support heating controlling units configured to control the at least one first heater and the second heater.

In accordance with an aspect of the invention, an apparatus by which a sample monitoring system is calibrated is provided and includes a first enclosure configured to enclose a probe body into which the sample and a calibration gas is drawn, a sensor coupled to the probe body and configured to sense a chemical composition of the sample and/or the calibration gas and at least one first heater configured to heat an interior of the first enclosure, a second enclosure configured to enclose a pump coupled to the probe body and configured to draw the sample and/or the calibration gas therein and a second heater configured to heat the pump, and a third enclosure configured to enclose a pump motor configured to control the pump and heating controlling units configured to control the at least one first heater for the first enclosure and the second heater for the pump.

In accordance with an aspect of the invention, an apparatus by which a sample monitoring system is calibrated is provided and includes a first enclosure configured to enclose a probe body into which the sample is drawn and into which a calibration gas is injected, a sensor coupled to the probe body and configured to sense a chemical composition of the sample and/or the calibration gas and at least one first heater configured to heat an interior of the first enclosure, a second enclosure configured to enclose a pump coupled to the probe body and configured to draw the sample therein and a second heater configured to heat the pump, and a third enclosure configured to enclose a pump motor configured to control the pump and heating controlling units configured to control the at least one first heater for the first enclosure and the second heater for the pump.

BRIEF DESCRIPTIONS OF THE DRAWINGS

The subject matter regarded as the invention is particularly pointed out and distinctly claimed in the claims at the conclusion of the specification. The foregoing and other aspects, features, and advantages of the invention are apparent from the following detailed description taken in conjunction with the accompanying drawings in which:

DETAILED DESCRIPTION OF THE INVENTION

Figure 1:
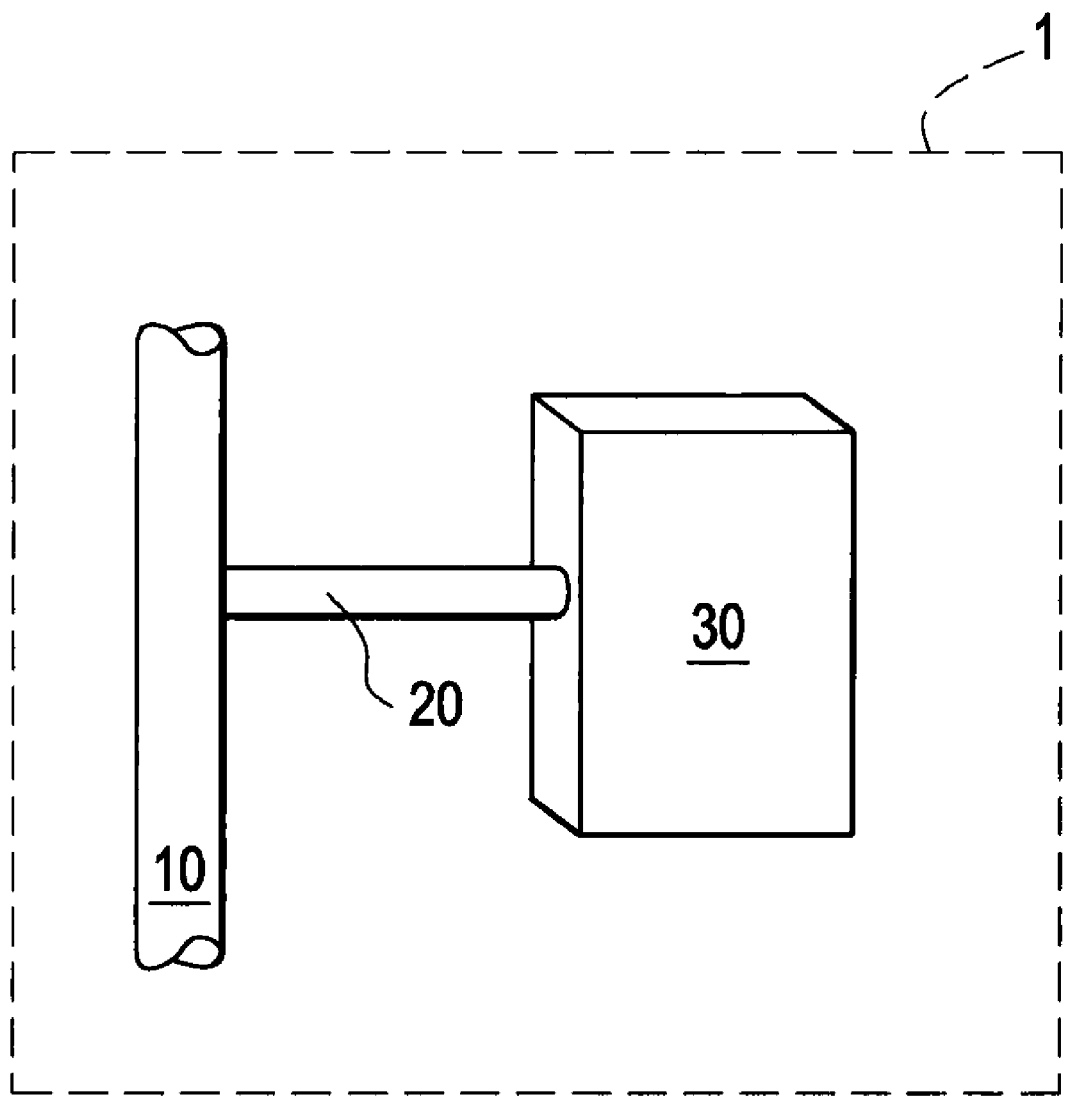
FIG. 1 is a schematic view of a power plant in which an exemplary apparatus for use in a sample monitoring system is installed.

With reference to FIG. 1, a power plant 1, such as a simple cycle power plant, a combined cycle power plant or a rankine cycle power plant, may include a natural gas power utility boiler from which exhaust is carried through an exhaust system 10. An extraction system 20 extracts a sample of the exhaust gases from the exhaust system 10. An apparatus 30 is provided for use in a monitoring of the sample on, e.g., a hot wet basis where no conditioning or drying of the sample occurs prior to the monitoring of the sample.

Figure 2:
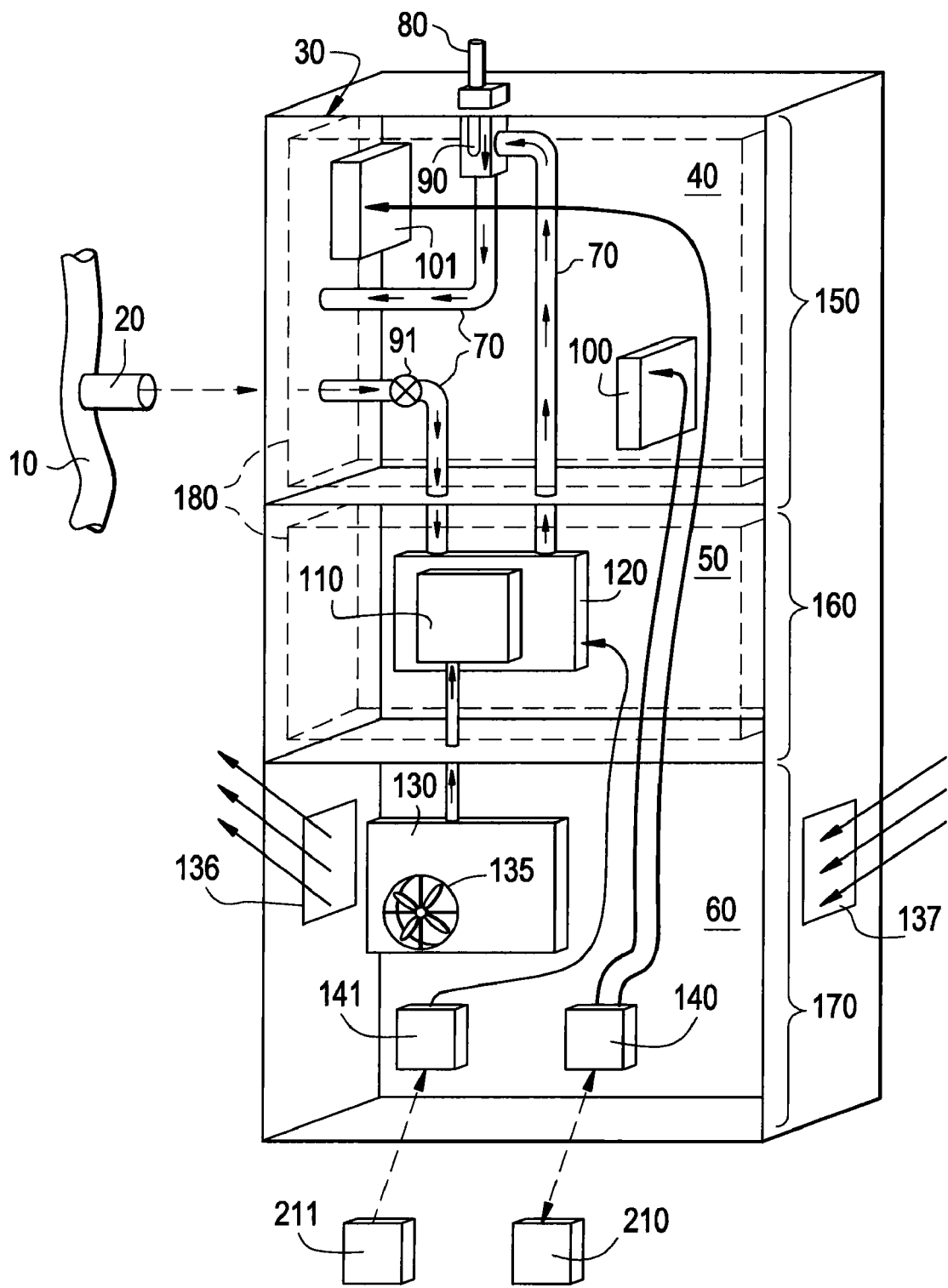
FIG. 2 is an enlarged perspective view of an exemplary interior of the apparatus of FIG. 1.

With reference to FIG. 2, the apparatus 30 includes a first enclosure 40 through which a portion 70 of the extraction system 20 extends. The portion 70 of the extraction system 20 may include sample tubing. The first enclosure 40 is configured to enclose a sensor 90 coupled to a probe body 80 and at least one first heater 100 and 101. The sample is drawn from the portion 70 and through the probe body 80. The sensor 90, being coupled to the probe body 80, is configured to sense a chemical composition of the sample. A needle valve 91 is used to adjust the sample flow rate to the sensor 90.

The sensor 90 may include a zirconium oxide oxygen sensor which is configured to sense an oxygen concentration, on a hot wet basis, within the sample. As such, in order to obtain reliable measurements, it is necessary to maintain the sample temperature during the sensing process.

To this end, the at least one first heater 100 and 101 is configured to heat an interior of the first enclosure 40 and may include two ceramic rubber heaters, as shown, which cooperate to provide redundant heating for the first enclosure 40. In an embodiment, one of the ceramic rubber heaters may be positioned within the first enclosure 40 proximate to a first side of the probe body 80 while the other ceramic rubber heater may be positioned proximate to another side of the probe body 80.

The apparatus 30 further includes a second enclosure 50, which is configured to enclose a pump 110 with a second heater 120, as well as a third enclosure 60, which is configured to enclose a pump motor 130 and solid state relays 140 and 141 by which the at least one first heater 100 and 101 and the second heater 120 are controlled. The pump 110 is configured to draw the sample through the portion 70 of the extraction system 20 and toward the sensor 90. The second heater 120 may include a cartridge-type heater and is configured to heat the pump 110 as an additional system provided for the maintenance of the sample temperature. The pump motor 130 provides a force necessary to transport the sample and includes a fan 135 to provide cooling. The fan 135 circulates air by drawing air through duct 137 into the third enclosure 60 and vents hot air through duct 136.

As shown in FIG. 2, the second enclosure 50 is adjacent to first enclosure 40 and the third enclosure 60 is adjacent to the second enclosure 50. The adjacencies of the first, second and third enclosures 40, 50 and 60 are, however, not limited to the illustrated arrangement and it is noted that other similar arrangements are possible. For example, the first, second and third enclosures 40, 50 and 60 may be laterally adjacent to one another and/or may be arranged in different positional orders. In any case, the apparatus 30 may further include first, second and third housings 150, 160 and 170 to each define a shape of the first, second and third enclosures 40, 50 and 60, respectively.

Insulation 180 is provided on at least interior surfaces of the first and second housings 150 and 160. The insulation 180 is configured to insulate at least the interior surfaces of the first and second housings 150 and 160 and to, therefore, also insulate the interiors of the first, second and third enclosures 40, 50 and 60 from one another. In accordance with an embodiment, the insulation 180 may include a ceramic fiber or some other suitable insulating material.

Figure 3:
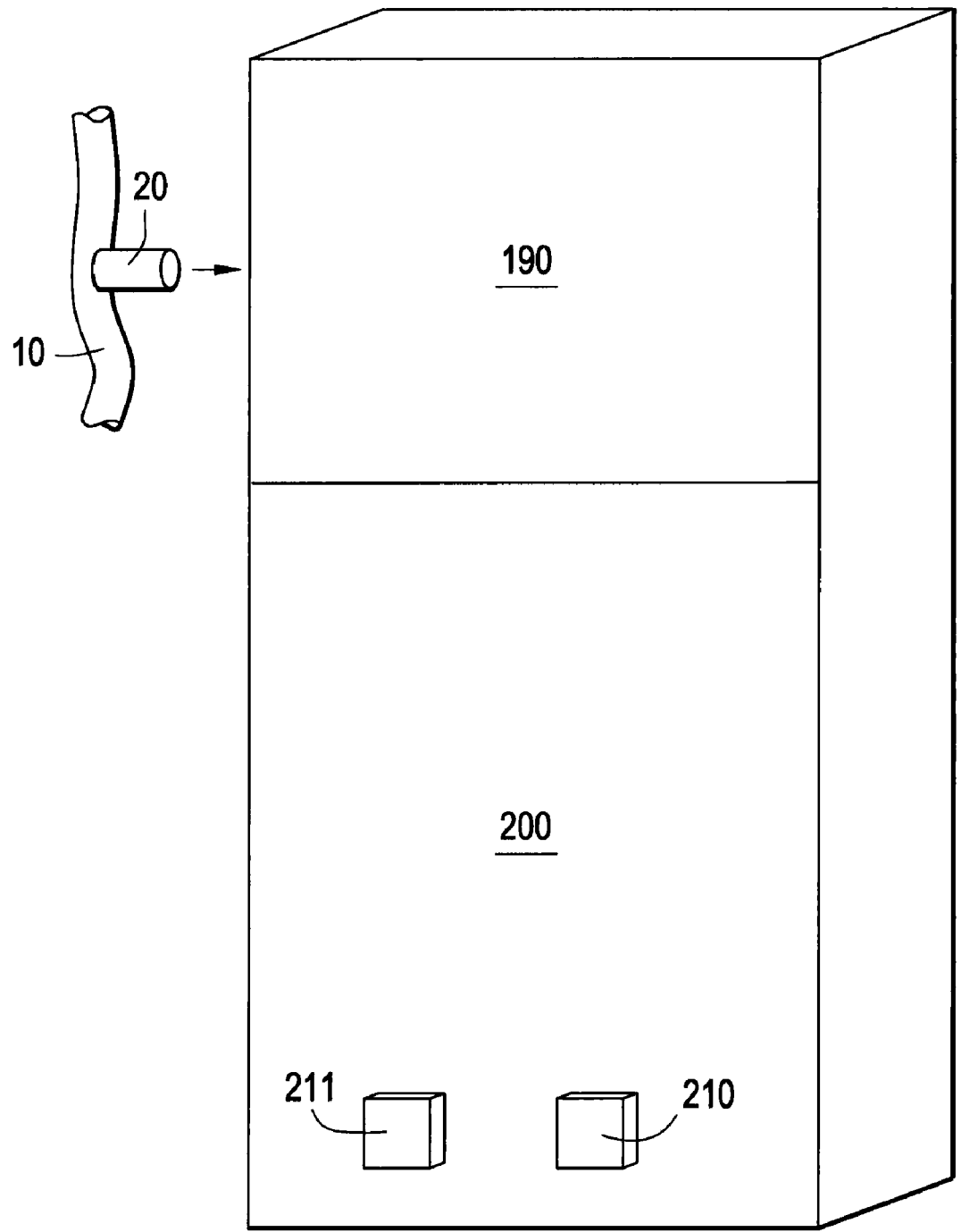
FIG. 3 is an enlarged perspective view of an exemplary exterior of the apparatus of FIG. 1.

With reference to FIG. 3, the apparatus 30 may further include a first cover 190, which is configured to cover the first enclosure 40, and a second cover 200, which is configured to cover the second and third enclosures 50 and 60. Of course, it is understood that a single cover may be used to cover each of the enclosures or that a third enclosure may be employed to separately cover the third enclosure 60.

Temperature controllers 210 and 211 are supported on the second cover 200. Each of the temperature controllers 210 and 211 is respectively connected to a corresponding solid state relay 140 and 141 and is configured to receive a user input as to a respective operation of the corresponding first heater 100, 101 and the second heater 120. In an embodiment, each of the temperature controllers 210 and 211 may include an input unit by which the user inputs instructions regarding, e.g., temperatures of the interior of the first enclosure 40 and the pump 110.

Thus, it may be seen that the temperature controllers 210 and 211 and the solid state relays 140 and 141 together form a heating controlling unit that controls the at least one first heater 100, 101 and the second heater 120. That is, operation and control of the first heater 100, 101 and the second heater 120, as is described above, is accomplished by way of the solid state relays (SSRs) 140, 141, which, in an embodiment, may be RoHS (Restriction of Hazardous Substances directive) compliant and the temperature controllers 211 and 210, which may also be RoHS compliant. As such, if the user indicates that the first heater 100 is to operate at a given temperature of, e.g., 145 degrees Celsius, the temperature controller 210 will control the heaters 100 and 101 to do so and, if either heater should fail, the other will continue to operate.

As a result of testing conducted on the apparatus 30, as described above, it has been seen that where the at least one of the first heaters 100 and 101, as controlled by the temperature controller 210, are set to 145 degrees Celsius, they cooperatively maintain a temperature range of about 85-103.3 degrees Celsius within the first enclosure 40. Meanwhile, it has also been seen that where the second heater 120, as controlled by the temperature controller 211, is set to 160 degrees Celsius, the insulation 180 of the second enclosure 50 allows a temperature within the third enclosure 60 to be maintained within a range of about 43-45 degrees Celsius.

In addition, it has been seen that exterior surface temperatures of the covers 190 and 200 and the housing 150 are also controlled and maintained within safe ranges. For example, near an edge of the upper surface of the cover 190 a maximum temperature has been shown to reach only about 44 degrees Celsius. Near a center of the upper surface of the cover 190 a maximum temperature has been shown to reach only about 48 degrees Celsius. A maximum temperature of a side of the housing 150 has been shown to reach only about 44 degrees Celsius, and a maximum temperature of a front of the cover 190 has been shown to reach only about 42 degrees Celsius.

In accordance with additional aspects, the apparatus 30, as described above, may be employed in a calibration operation. Here, calibration gas is either drawn into the probe body 80 by the pump 110 or is injected directly to the sensor 90. The calibration gas is then sampled by the sensor 90 to determine if the various features described above are operating normally.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof Therefore, it is intended that the disclosure not be limited to the particular exemplary embodiment disclosed as the best mode contemplated for carrying out this disclosure, but that the disclosure will include all embodiments falling within the scope of the appended claims.

We claim:

1. An apparatus for use in a sample monitoring system, comprising:
    a first enclosure configured to enclose a probe body into which the sample can be drawn, a sensor coupled to the probe body and configured to sense a chemical composition of the sample, at least one first heater configured to heat an interior of the first enclosure;
    a second enclosure enclosing a pump and a second heater configured to heat the pump; and
    a third enclosure configured to enclose a pump motor configured to control an operation of the pump and to support heating controlling units configured to control the at least one first heater and the second heater; and
    tubing running from an external source through the first enclosure to the pump in the second enclosure and from the pump to the probe body, the pump being configured to draw the sample from the external source to the sensor coupled to the probe body.

2. The apparatus according to claim 1, wherein the second enclosure is adjacent to the first enclosure and the third enclosure is adjacent to the second enclosure.

3. The apparatus according to claim 1, further comprising first, second and third housings each of which respectively defines a shape of the first, second and third enclosures.

4. The apparatus according to claim 3, further comprising insulation configured to insulate the interiors of the first, second and third enclosures from one another.

5. The apparatus according to claim 4, wherein the insulation comprises ceramic fiber.

6. The apparatus according to claim 3, further comprising first and second covers respectively configured to cover the first enclosure, and the second and third enclosures.

7. The apparatus according to claim 6, further comprising temperature controllers, supported on the second cover, each of which is respectively coupled to the heating controlling unit and configured to receive a user input as to an operation thereof.

8. The apparatus according to claim 7, wherein each of the temperature controllers respectively controls the at least one first heater and the second heater.

9. The apparatus according to claim 7, wherein the heating controlling unit comprises a solid state relay (SSR).

10. The apparatus according to claim 1, wherein the sensor comprises a zirconium oxide oxygen sensor.

11. The apparatus according to claim 1, wherein each of the at least one first heaters comprises a ceramic rubber heater.

12. The apparatus according to claim 11, wherein the ceramic rubber heaters are disposed proximate the sensor in the first enclosure.

13. The apparatus according to claim 1, wherein the second heater comprises a cartridge-type heater.

14. The apparatus according to claim 1, wherein the pump motor provides motive force for sample transport to the sensor and comprises a fan configured to circulate air in the third enclosure.

15. A power plant, comprising;
an exhaust system through which exhaust gases generated in the power plant are exhausted;
an extraction system, coupled to the exhaust system, to extract a sample of the exhaust gases from the exhaust system; and
the apparatus of claim 1 coupled to the extraction system to monitor a chemical composition of the sample.

16. An apparatus by which a sample monitoring system is calibrated, comprising:
a first enclosure configured to enclose a probe body into which the sample can be drawn, a sensor coupled to the probe body and configured to sense a chemical composition of the sample, and at least one first heater configured to heat an interior of the first enclosure;
a second enclosure configured to enclose a pump that is configured to draw the sample through the first enclosure from an external source to the probe body, and a second heater configured to heat the pump; and
a third enclosure configured to enclose a pump motor configured to control the pump and heating controlling units configured to control the at least one first heater for the first enclosure and the second heater for the pump.

17. An apparatus by which a sample monitoring system is calibrated, comprising:
a first enclosure configured to enclose a probe body into which the sample is drawn and into which a calibration gas is injected, a sensor coupled to the probe body and configured to sense a chemical composition of the sample or the calibration gas, and at least one first heater configured to heat an interior of the first enclosure;
a second enclosure configured to enclose a pump configured to draw the sample from tubing from an external source through the second enclosure to the probe body in the first enclosure, and a second heater configured to heat the pump; and
a third enclosure configured to enclose a pump motor configured to control the pump and heating controlling units configured to control the at least one first heater for the first enclosure and the second heater for the pump.

* * * * *